(12) United States Patent
Berendt

(10) Patent No.: US 7,648,599 B2
(45) Date of Patent: Jan. 19, 2010

(54) METHOD OF PREPARING NICKEL TITANIUM ALLOY FOR USE IN MANUFACTURING INSTRUMENTS WITH IMPROVED FATIGUE RESISTANCE

(75) Inventor: Carl J. Berendt, Afton, OK (US)

(73) Assignee: Sportswire, LLC, Langley, OK (US)

( * ) Notice: Subject to any disclaimer, the term of this patent is extended or adjusted under 35 U.S.C. 154(b) by 625 days.

(21) Appl. No.: 11/225,223

(22) Filed: Sep. 13, 2005

(65) Prior Publication Data

US 2007/0072147 A1    Mar. 29, 2007

(51) Int. Cl.
*C22F 1/10* (2006.01)
(52) U.S. Cl. ........................ 148/563; 148/676
(58) Field of Classification Search ................ None
See application file for complete search history.

(56) References Cited

U.S. PATENT DOCUMENTS

| | | | | |
|---|---|---|---|---|
| 3,652,969 | A | * | 3/1972 | Willson et al. .............. 337/140 |
| 4,086,769 | A | * | 5/1978 | Smith .......................... 60/527 |
| 4,707,196 | A | | 11/1987 | Honma et al. |
| 4,899,543 | A | * | 2/1990 | Romanelli et al. ............ 60/527 |
| 5,464,362 | A | | 11/1995 | Heath et al. |
| 5,762,541 | A | | 6/1998 | Heath et al. |
| 5,984,679 | A | | 11/1999 | Farzin-Nia et al. |
| 6,149,501 | A | | 11/2000 | Farzin-Nia et al. |
| 6,315,558 | B1 | | 11/2001 | Farzin-Nia et al. |
| 6,428,317 | B1 | | 8/2002 | Abel |
| 6,431,863 | B1 | | 8/2002 | Sachdeva et al. |
| 6,596,102 | B2 | * | 7/2003 | Homma ...................... 148/561 |
| 6,626,937 | B1 | | 9/2003 | Cox |
| 2003/0199236 | A1 | | 10/2003 | Aloise et al. |
| 2004/0171333 | A1 | | 9/2004 | Aloise et al. |
| 2004/0193104 | A1 | | 9/2004 | Jervis |
| 2004/0216814 | A1 | | 11/2004 | Dooley et al. |
| 2005/0059994 | A1 | | 3/2005 | Walak et al. |
| 2005/0090844 | A1 | | 4/2005 | Patel et al. |
| 2005/0198777 | A1 | | 9/2005 | Mabe |

FOREIGN PATENT DOCUMENTS

EP    EU 06254743.5    12/2006
GB    2106190 A    *    4/1983

* cited by examiner

*Primary Examiner*—George Wyszomierski
(74) *Attorney, Agent, or Firm*—Gable Gotwals

(57) ABSTRACT

A method of treating Nitinol to train the structure thereof to remain in the martensite state, including the steps of subjecting the Nitinol to a strain and while subjected to the strain, thermally cycling the Nitinol between a cold bath of about 0° C. to 10° C. and a hot bath of about 100° C. to 180° C. for a minimum of about five cycles.

12 Claims, 6 Drawing Sheets

METHOD OF PREPARING NICKEL TITANIUM ALLOY FOR USE IN MANUFACTURING INSTRUMENTS WITH IMPROVED FATIGUE RESISTANCE

REFERENCE TO PENDING APPLICATIONS

This application is not related to any pending domestic or international patent applications.

REFERENCE TO MICROFICHE APPENDIX

This application is not referenced in any microfiche appendix.

BACKGROUND OF THE INVENTION

1. Field of the Invention

The present invention is related generally to a method of treating a nickel titanium alloy, known as Nitinol, for use in manufacturing instruments having improved resistance to cyclic fatigue failure. As a particular application, the invention is related to preparation of Nitinol wire blanks for use in manufacturing endodontic files having improved resistance to cyclic fatigue failures.

2. Background of the Invention

Many medical applications take advantage of the properties of Nitinol, a nickel and titanium alloy. Nitinol (an acronym for Nickel Titanium Naval Ordinance Laboratory) exhibits several useful properties such as shape memory, by which a Nitinol component returns to a previously memorized shape after being forced into a second shape. Nitinol also exhibits superelasticity, meaning that a Nitinol component may be deformed elastically to a very large extent by strain without reducing its ability to return to the its original shape after the strain has been removed. One drawback of Nitinol, however, is that in certain configurations it is not very resistant to fatigue, i.e. repeated cyclic strains.

In the specification, claims and abstract that follows the term "martensite" means an alloy in a substantially martensitic phase or condition and the term "austenite" means an alloy in a substantially austenitic phase or condition. Therefore the term "martensite state" means a "substantially martensite state" and the term "austenite state" means a "substantially austenite state".

The present invention is directed to a method of preparing Nitinol so that it can be used to manufacture instruments that retain the martensitic state at the operating temperature with corresponding greater resistance to cyclic fatigue failure.

The present invention is further directed to a method of forming a dental device comprising the steps of forming the device of Nitinol having an impressed memorized shape, wherein the memorized shape is a shape the element assumes when in an operational configuration. The element is treated so that it is substantially martensite phase stabilized under expected operating conditions.

Nitinol is an alloy which was developed to achieve improved elasticity and other enhanced mechanical properties. Nitinol also possesses shape memory properties that are well suited for medical and dental applications. Elements constructed of Nitinol may be formed in a first "memorized" shape to which they will return after deformation. That is, when such a Nitinol element has been deformed, raising a temperature of the element above a critical temperature causes the element to revert to its memorized shape.

As would be understood by those of skill in the art, Nitinol alloys can exist in one of two different temperature-dependent crystal structures. At lower temperatures, Nitinol is martensitic, meaning that its structure is composed of self-accommodating twins, in a zigzag-like arrangement. Martensite is soft and malleable, and can be easily deformed by de-twinning the structure via application of strain. At higher temperatures, above a critical temperature of the alloy, Nitinol is austenitic. Austenite is a strong and hard phase of the alloy, exhibiting properties similar to those of titanium, and is characterized by a much more regular crystalline lattice structure. Nitinol alloys can also undergo a phase change as a result of the application of a strain. For example, an element in the austenitic phase can be bent so that at high strain locations the alloy becomes martensitic. If the alloy is designed to have an unstable martensite phase at the operating temperature, removal of the strain results in a reverse transformation that straightens the bending.

3. Description of the Prior Art

For background information relating to the subject matter of this invention, reference may be had to the following issued United States patents and publications:

| PAT. NO. | INVENTOR(S) | ISSUE DATE | TITLE |
|---|---|---|---|
| 5,464,362 | Heath et al. | Nov. 07, 1995 | Endodontic Instrument |
| 5,762,541 | Heath et al. | Jun. 09, 1998 | Endodontic Instrument |
| 5,984,679 | Farzin-Nia et al. | Nov. 16, 1999 | Method of Manufacturing Superelastic Endodontic Files and Files Made Therefrom |
| 6,149,501 | Farzin-Nia et al. | Nov. 21, 2000 | Superelastic Endodontic Instrument, Method of Manufacture, and Apparatus Therefor |
| 6,315,558 | Farzin-Nia et al. | Nov. 13, 2001 | Method of Manufacturing Superelastic Endodontic Files and Files Made Therefrom |
| 6,428,317 | Abel | Aug. 06, 2002 | Barbed Endodontic Instrument |
| 6,431,863 | Sachdeve et al. | Aug. 13, 2002 | Endodontic Instruments Having Improved Physical Properties |
| 6,626,937 | Cox | Sep. 30, 2003 | Austenitic Nitinol Medical Devices |
| 2003/0,199,236 | Aloise et al. | Oct. 23, 2003 | Method of Manufacturing An Endodontic Instrument |
| 2004/0,171,333 | Aloise et al. | Sep. 02, 2004 | Method of Manufacturing An Endodontic Instrument |
| 2004/0,193,104 | Jervis | Sep. 30, 2004 | Bendable, Reusable Medical Instruments With Improved Fatigue Life |
| 2004/0,216,814 | Dooley et al. | Nov. 04, 2004 | Shape Memory Alloy Articles With Improved Fatigue Performance and Methods Therefore |

-continued

| PAT. NO. | INVENTOR(S) | ISSUE DATE | TITLE |
|---|---|---|---|
| 2005/0,059,994 | Walak et al. | Mar. 17, 2005 | Fatigue Resistant Medical Devices |
| 2005/0,090,844 | Patel et al. | Apr. 28, 2005 | Long Fatigue Life Nitinol |

BRIEF SUMMARY OF THE INVENTION

The present invention relates to manufacturing methods of achieving improvements in the fatigue resistance of Nitinol instruments. The methods involve thermal and mechanical rearrangement and stabilization of a cold-working-induced martensite state in Nitinol instruments, such that the Nitinol parts are in a martensitic state thermodynamically at operating temperatures, with the characteristic austenite finish temperature of the Nitinol metal, measured by a differential scanning calorimeter, being above the part's operating temperature and in which the ultimate tensile strength to upper plateau stress ratio in a tensile test is 2.8 or higher. A series of fatigue performance tests have indicated that the improved martensitic Nitinol wire blanks and instruments made therefrom, have useable lives up to seven times longer than the conventional austenitic ones under the same operating conditions.

Fatigue failure is a common problem in endodontic instruments. Improvements in fatigue resistance of Nitinol is desirable since it provides increased fatigue life and better fatigue life predictability. Existing methods have not adequately addressed the effects of Nitinol processing on fatigue life and fatigue life improvements have been limited to a relatively small range (generally less than 50% improvement). The present invention provides a novel method to increase the useable life of endodontic instruments by as much as seven times.

The starting material for use in the method of this invention is a Nitinol composition consisting of 55.8+/−1.5 wt. % nickel (Ni); 44.2+/−1.5 wt. % titanium (Ti); and trace elements including iron (Fe), chromium (Cr), copper (Cu), cobalt (Co), oxygen (O), hydrogen (H), and/or carbon (C), generally less than 1 wt. %.

The invention is practiced by starting with Nitinol in an austenitic state. This material is 45+/−5% cold worked (cross-sectional area reduction) at finish diameter followed by final straightening anneal at 500 to 600° C. for 60 to 120 seconds. With the material in the martensitic state it is 35+/−5% cold worked at a finished diameter. It is then subjected to final straightening anneal at 400 to 475° C. for 120 to 300 seconds and then thermal cycled under constraint elongation of 1 to 4% between cold (0 to 10° C.) and hot (100 to 180° C.) for 3 to 5 times.

The resultant material then has a tensile modulus as follows: Austenitic conditions: Average~10 Mpsi and Martensitic conditions: Average~6 Mpsi ("Mpsi" meaning "million pounds per square inch").

The material also has the ultimate tensile strength to the upper plateau stress ratio as follows: Austenitic conditions: Average~2.5; and Martensitic conditions: Average~3.0. The austenite finish temperature as measured by a differential scanning calorimeter is an average ~15° C. and the martensite finished temperature measured in the same way is an average~52° C.

Nitinol wire blanks tested at room temperature in austenitic conditions averaged 83.5 seconds to fracture while, employing the same test procedures, in martensitic conditions the Nitinol wire blanks averaged 562.4 seconds to fracture, thus an approximately 673% improvement.

Endodontic files tested at 37° C. (body temperature) under austenitic conditions averaged 85.7 seconds to fracture while with the same test, under martensitic conditions the files averaged 261 seconds to fracture, thus a greater than 300% improvement.

A more complete understanding of the invention will be obtained from the following detailed description of the preferred embodiments and claims, taken in conjunction with the attached drawings.

BRIEF DESCRIPTION OF THE DRAWINGS

FIG. 9 shows a Nitinol endodontic file subjected to a bending fatigue test.

DETAILED DESCRIPTION OF THE PREFERRED EMBODIMENTS

Figures 1, 2:
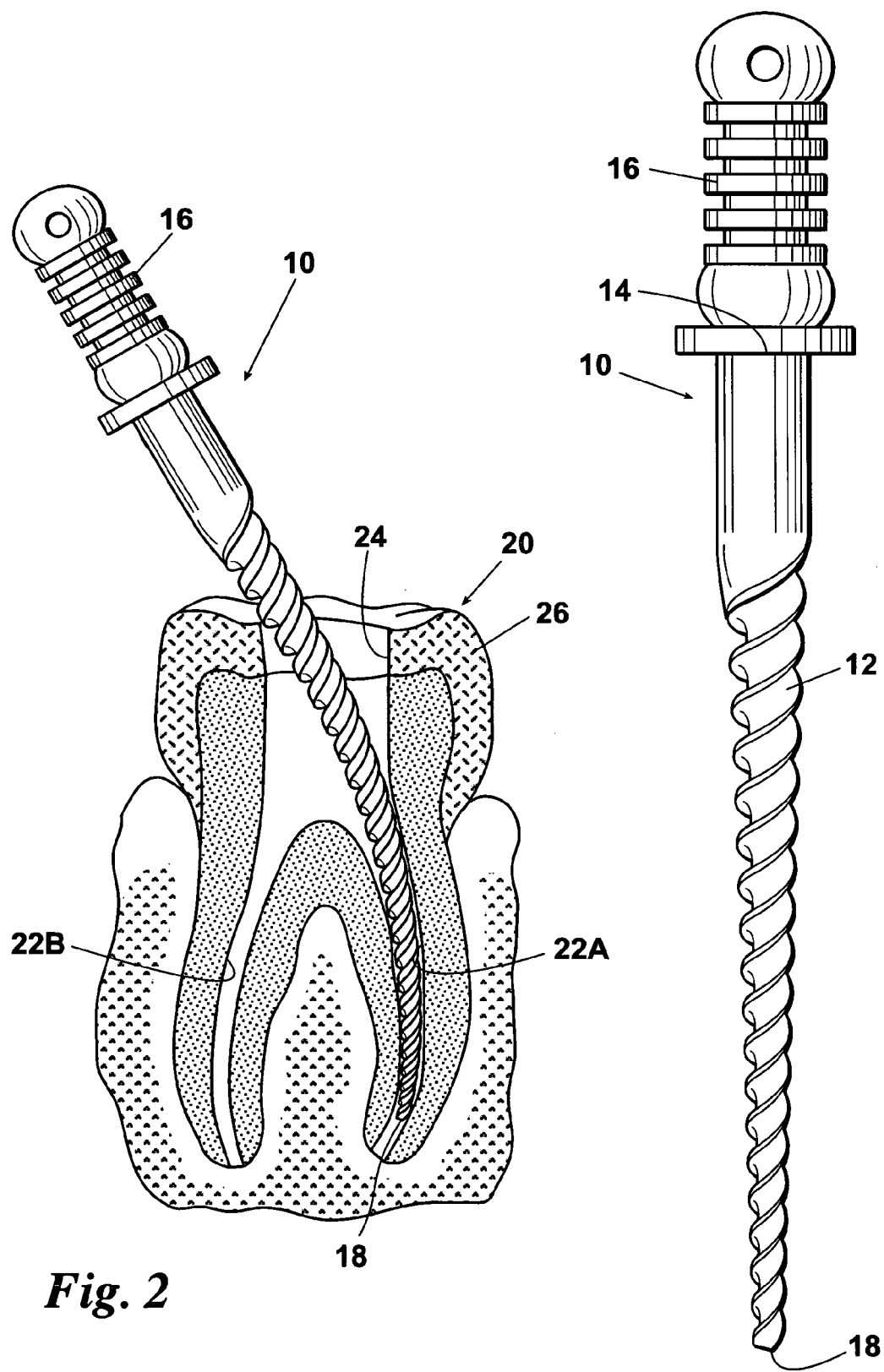
FIG. 1 is an elevational view of a typical endodontic file showing the lower portion thereof, that is, the stem of the file having circumferential grooves formed on the outer surface to form circumferential cutting/scraping edges. The invention herein is a method of providing a Nitinol alloy having improved resistance to fatigue failure. The file of FIG. 1 is illustrated as an example of a medical device that can be successfully manufactured by employing Nitinol material produced by practicing the invention herein.
FIG. 2 is an elevational cross-sectional view of a molar human tooth showing the root system and the coronal area penetrated by a hole to expose the root canal system. Shown positioned within one of the root canals is the endodontic file as illustrated in FIG. 1. The endodontic file is subjected to substantial bending and torsional stress as it is used in the process of cleaning and shaping a root canal. The invention herein is concerned with the material of which the endodontic file is made to significantly increase resistance to cyclic fatigue.

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Endodontic file |
| 12 | Shaft portion |
| 14 | Proximal end |
| 16 | Handle |
| 18 | Distal end |
| 20 | Tooth |
| 22A,B | Roots |
| 24 | Hole |
| 26 | Crown |
| 28 | Roll of Nitinol wire in Austenite form |
| 30 | Nitinol wire |
| 32 | Cold water shower |
| 34 | Cold water tank |
| 36 | First turn wheel |
| 38 | Second turn wheel |
| 40 | Third turn wheel |
| 42 | Hot water tank |
| 44 | Fourth turn wheel |
| 46 | Treated wire |
| 48 | Finish spool |
| 50 | Austenite form |
| 52 | Twinned martensite form |
| 54 | Deformed martensite |
| 56 | Nitinol austenite state |
| 57 | Nitinol deformed austenite state |
| 58 | Nitinol twinned martensite state |
| 60 | Nitinol deformed martensite state |
| 62 | Spool of Nitinol wire |
| 64 | Untreated Nitinol Wire |
| 66 | Annealing oven |
| 68 | Die |
| 70 | Die |
| 72 | Die |
| 74 | Die |
| 76 | Wire holding clamp |
| 78 | Test machine stand |
| 80 | Nitinol wire |
| 82 | Wheel |
| 84 | Axis |
| 86 | Dowel pins |
| 88 | Mandrel |
| 90 | Deflection block |
| 92 | Arcuate surface |
| 94 | Space |
| 96 | Groove |
| 98 | Rotating instrument holder |
| 100 | Chuck |
| 102 | Endodontic instrument |
| 104 | Nozzle |
| 106 | Water or air |

FIGS. 1 and 2 illustrate an endodontic file. An endodontic file is a good example of a product that is subject to fatigue failure and wherein a failure of the product is a serious event. Thus the endodontic file is illustrated as an example of a product that can be successfully manufactured by the methods of this invention. FIG. 1 is an elevational view of an endodontic file generally indicated by the numeral 10 that has an elongated shaft portion 12 with a proximal end 14 to which is secured a small cylindrical handle 16, normally made of plastic by which the file shaft portion 12 can be inserted into and removed from the root canal of the tooth. The handle 16 is configured to be positioned between the thumb and forefinger of an endodontist to facilitate manipulation of the file in the root canal and simultaneously rotation of the file. The distal end 18 of file 10 is of reduced diameter compared to the proximal end and is typically pointed.

FIG. 2 illustrates a typical tooth 20, in this case is a molar, having plural roots 22A and 22B, that in a healthy tooth are filled with pulpal material. When this pulpal material becomes infected the tooth is deemed to be abscessed and the pressure generated by the abscess causes an intense tooth ache. Endodontists treat this malady by performing a root canal procedure in which the root canals 22A and 22B are cleaned of pulpal material. To do that a hole 24 is drilled in the tooth crown 26 to provide access to the root canals 22A and 22B. An endodontist inserts a file 10 through the hole 24 into the canals to facilitate removal of the pulpal material. FIG. 2 shows the tooth free of pulpal material.

The endodontic tool 10 of FIGS. 1 and 2 is, as previously stated, an example of a type of instrument that requires a high degree of flexibility along with resistance to torque fatigue. It can be seen that if in the process of treating a root canal 22A a lower portion of dental file 10 is broken off in the canal then the endodontist is faced with a serious problem, particularly if the root canal beneath the broken off portion has not been thoroughly cleaned of infected pulpal material. It is therefore important in manufacturing endodontic files to provide files that have great flexibility and at the same time high fatigue resistance.

It is important to understand that the endodontic file shown in FIGS. 1 and 2 and the use thereof is by example only to establish the need for structural material for use in constructing the shaft portion 12 to achieve high flexibility and, most importantly, high fatigue resistance. It is important to understand that the invention herein does not concern endodontic files per se but concerns methods of treating material, and particularly treating an alloy to produce a metal having ideal characteristics for use in the manufacture of endodontic tools and other similar medical and non-medical devices that require high fatigue resistance.

It has been learned that an ideal material for manufacturing tools requiring flexibility and fatigue resistance is an alloy of nickel and titanium. This alloy is commonly referred to in industry as "Nitinol". The expression "Nitinol" will be used herein rather than "nickel/titanium alloy". The preferred composition of Nitinol is about 55.8%, +/−1.5%, by weight of nickel combined with 44.2%, +/−1.5%, by weight of titanium. In addition to these two primary components of the alloy, trace elements including iron (Fe), chromium (Cr), copper (Cu), cobalt (Co), oxygen (0), hydrogen (H), carbon (C) are typically included, the trace elements generally totaling less than about 1% by weight of the finished alloy.

Figure 5:
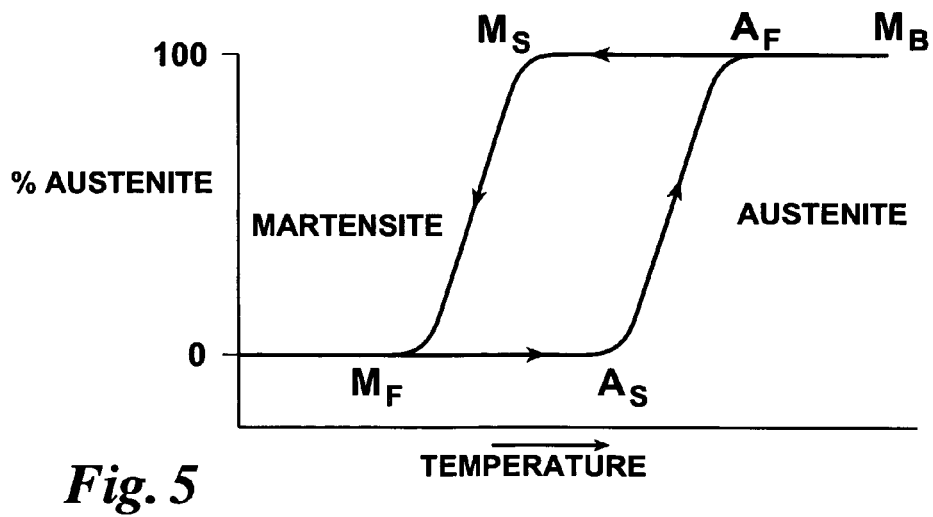
FIG. 5 is a graph illustrating the hysteresis effect as Nitinol is transitioned between martensite and austenite phases.

Nitinol as an alloy exists in two naturally occurring forms, that is, in the austenite form and in the martensite form. FIG. 5 is a graph showing transitions that occur in Nitinol as the form of the metal changes between austenite and martensite. As illustrated in this graph, within a given temperature range, the alloy can stabilize as either martensite or austenite. The graph in FIG. 5 shows that starting from a given temperature designated as martensite finish temperature "$M_f$", as the temperature increases the point is reached where the austenite form starts, designated as austenite start temperature "$A_s$".

The austenite form increases as a percent of the alloy rapidly as the temperature increases to the austenite finish state, designated as austenite finish temperature $A_f$. The alloy will remain in the 100% austenite form even as the temperature increases to a temperature indicated as $M_d$ which is the highest temperature at which strain induced martensite can exist. It is an essential aspect of the present invention that Nitinol in the martensite form can demonstrate significantly improved fatigue resistance.

The invention is practiced by starting with Nitinol in an austenitic state. This material is 45+/−5% cold worked followed by final straightening anneal at 500 to 600° C. for 60 to 120 seconds. With the material in the martensitic state it is 35+/−5% cold worked at a finished diameter. It is then subjected to final straightening anneal at 400 to 475° C. for 120 to 300 seconds and then thermal cycled under constraint elongation of 1 to 4% between cold (0 to 10° C.) and hot (100 to 180° C.) for 3 to 5 times. The resultant material then has a tensile modulus as follows: Austenitic conditions: Average~10 Mpsi and Martensitic conditions: Average~6 Mpsi. The material has an ultimate tensile strength as follows: Austenitic conditions: Average~2.5; and Martensitic conditions: Average~3.0. The austenite finish temperature as measured by a differential scanning calorimeter is an average~15° C. and the martensite finished temperature measured in the same way is an average~52° C.

As previously stated, FIG. 5 is a graph illustrating a typical phase change temperature hysteresis curve for Nitinol. The austenite phase in the alloy is plotted as a function of the temperature, with several important transition temperatures marked. $A_s$ indicates the temperature at which the austenite starts and $A_f$ indicates the temperature wherein the alloy is 100% in the austenite phase, that is, the austenite transition is finished. $M_s$, and $M_f$ indicate the martensite start and finish temperatures, that is where the transition to martensite starts and finishes. It is apparent that the two transformations do not occur at the same temperature. Rather, a hysteresis loop exists corresponding to the phase transformation. In addition, a $M_d$ temperature exists, indicating the highest temperature at which strain induced martensite can exist, i.e., the temperature above which martensite can not be induced by strain. "Strain", "stress" and "deformation" are used interchangeably in this context. As would be understood by those skilled in the art, the specific temperatures at which Nitinol transitions occur are very sensitive to small variations in the alloy's content of nickel, titanium and any other trace elements. Nitinol's properties thus can be tailored for specific applications by controlling the alloy's composition. However, manipulation of Nitinol alloy content is not a subject of this invention.

Figure 4:
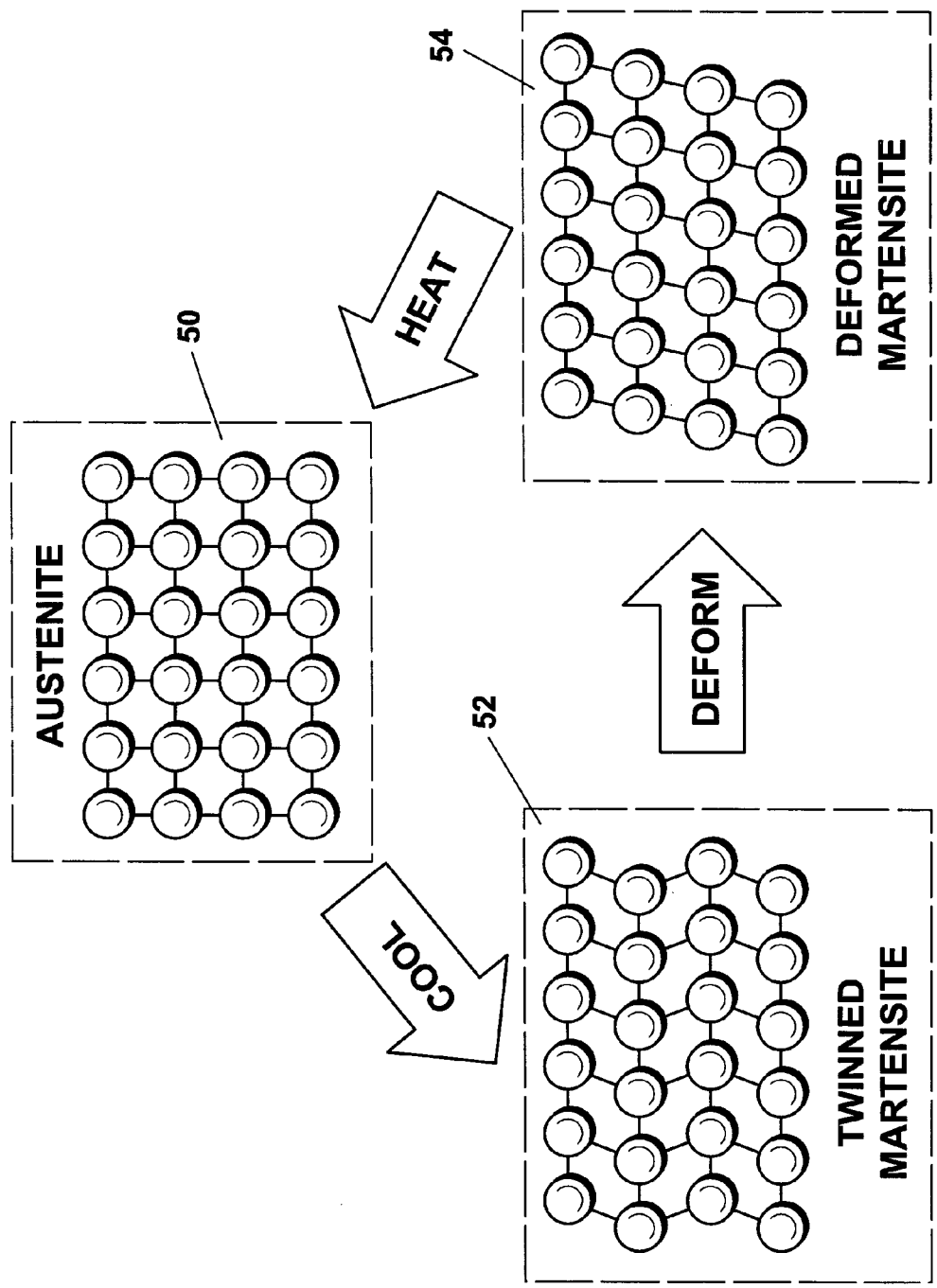
FIG. 4 illustrates diagrammatically the transitions of Nitinol between austenite and martensite phases in response to changes in temperature and deformation.

FIG. 4 diagrammatically illustrates the transition of Nitinol between the austenite form and the martensite form. The upper box 50 shows diagrammatically the arrangement of atoms of the alloy in an orderly fashion in which the alloy is in the austenite form. As the temperature of the alloy cools, the atomic structure changes from the initial orderly structure to a twinned martensite arrangement as shown in the lower left box 52. In this twinned martensite form and without a significant change in temperature, the alloy can be subject to deformation, particularly caused such as by stretching, so that it is transformed into a state indicated as "deformed martensite" or "de-twinned martensite" indicated by the lower right box 54. The alloy can remain in such state until heat is applied to reach the level of the austenite start ($A_s$) as shown in FIG. 5. As further heat is applied the alloy will then return to the 100% austenite state.

The shape memory and superelasticity properties of Nitinol may be understood in terms of the phase transformations the alloy undergoes under various conditions. As described above, shape memory refers to the ability to restore an originally memorized shape of a deformed Nitinol sample by heating it. FIG. 4 is a graph of temperature versus deformation illustrating the shape memory effect. An austenitic alloy element 50 has a shape represented by block 50 entitled "AUSTENITE" at a temperature above the $A_f$ temperature. The alloy is heated to a temperature above the $A_f$ temperature and formed into this desired shape. This causes the alloy to memorize the desired shape. As the temperature is lowered below the $M_s$ temperature, the alloy moves to the condition represented by the block 52 entitled "TWINNED MARTENSITE". If a strain is applied to the alloy element to deform it will take the condition identified by block 54 entitled "DEFORMED MARTENSITE" and will retain its shape even after the deformation inducing strain has been removed. Then, if the alloy is again heated to a temperature above the $A_f$ temperature, a thermoelastic phase transformation takes place and the element returns to its memorized, AUSTENITE shape of block 50 regaining its strength and rigidity.

An essential aspect of this invention is a system and method for transforming otherwise austenitic Nitinol, such as can occur in the form of wire, into a semi-stable martensite form. When in such martensite form the alloy can be manufactured into an implement, such as, by example, an endodontic file as illustrated in FIGS. 1 and 2.

Figure 3:
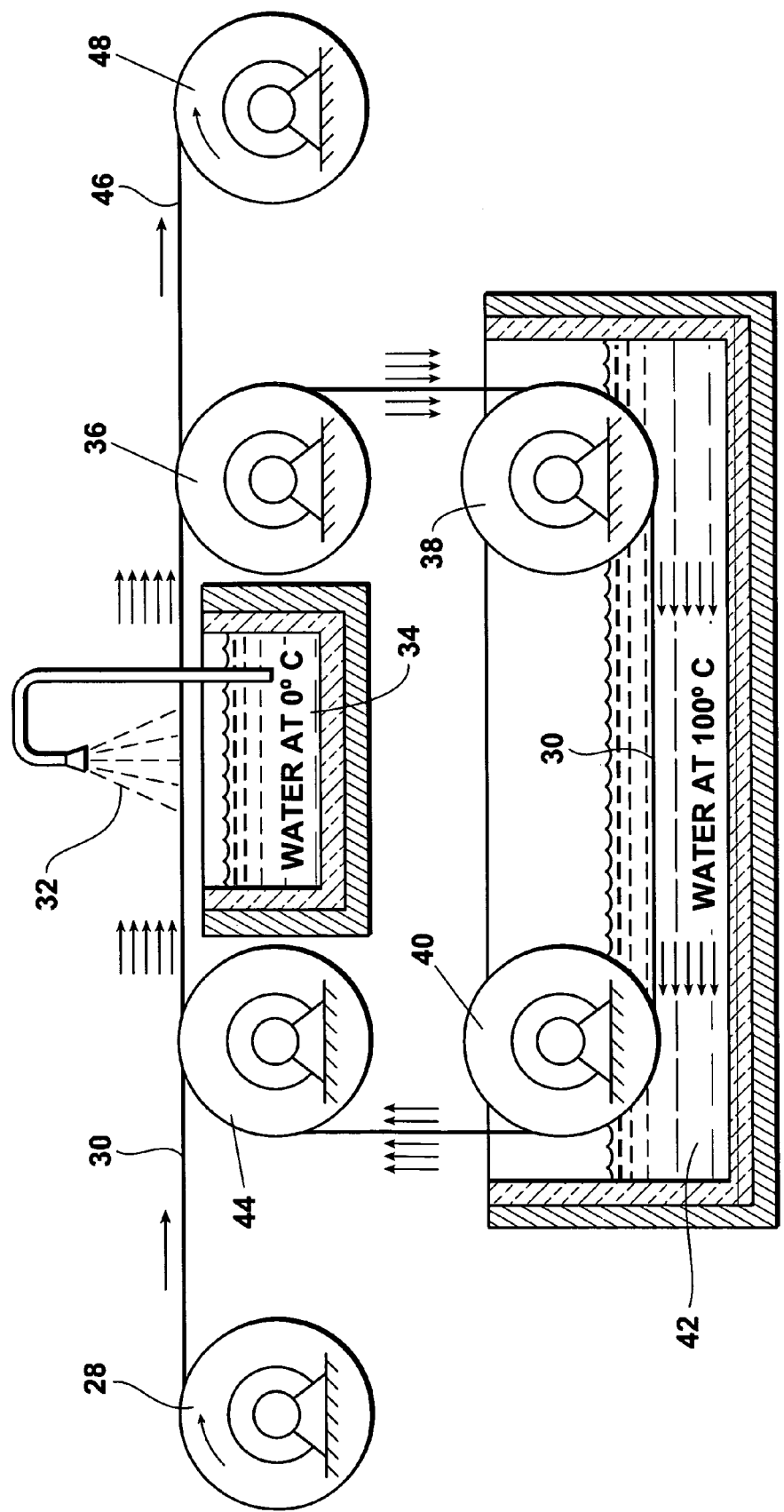
FIG. 3 is a diagrammatic illustration of steps employed in practicing the invention here to treat Nitinol wire so that it can be employed for producing instruments having greatly improved resistance to cyclic fatigue.

FIG. 3 illustrates a method of this invention of training Nitinol wire to retain the martensite state which may also be referred to as a "de-twinned martensite" state. In FIG. 3, a roll of Nitinol wire is indicated by the numeral 28. The Nitinol wire 30 passes through a cold water shower 32 that exists over a cold water tank 34. The wire 30 after passing through the shower 32 and being cooled to the temperature of about 0° C. to 10° C., passes over a first turn wheel 36 and bends over a second turn wheel 38. The wire 30 travels horizontally to a third wheel 40. Between wheels 38 and 40 wire 30 moves through hot water tank 42 wherein the temperature of the water is about 100° C. to 180° C. Out of the tank the wire 30 passes over a fourth turn wheel 44 to repeat the process.

From turn wheel 44 wire 30 passes back again through cold water shower 32, over first turn wheel 36, second turn wheel 38, through hot water tank 42, passed third turn wheel 40 and back again over fourth turn wheel 44. Wire 30 repeats this route a plurality of times, and preferably about four (4) or five (5) times. Thus, as shown in FIG. 3, the wire 30 from reel 28 is cycled four or five times between cold water shower 32 at about 0° C. to 10° C. and hot water tank 42 at about 100° C. to 180° C. After making four or five passages through the cold water shower and hot water tank the treated wire 46 passes to a finish spool 48. Wire from finish spool 48 is then in condition to be used to manufacture products, specifically instrumentation or other products that require a high degree of flexibility combined with an unusually high fatigue resistance characteristic.

Referring again to FIG. 4, the austenite atomic arrangement is illustrated in block 50. This illustration is diagrammatic and intended to be pictorial and is only representative of the form of the Nitinol when in the austenite state. When the austenite form 50 of FIG. 4 is cooled, the form of the Nitinol alloy takes an atomic arrangement termed the twinned martensite as indicated by block 52. When the Nitinol wire is in the twinned martensite form 52 and is subjected to deformation, particularly to stretching, the deformed martensite takes an atomic structure pictorially represented by block 54. Therefore, referring back to FIG. 3, it is important that the wire 30 be subjected to a deformation as it makes about four or five loops around wheels 36, 38, 40 and 44. Such deformation is most easily achieved by the application of strain on the wire of between 1 to 10%. This can be achieved by applying torque to finish spool 48. Thus, as wire 30 passes through the cold water shower 32 and hot water tank 42 approximately four or five times, it is constantly under tension deformation. Thus the Nitinol wire wound onto finish spool 38 is in the deformed martensite state.

Shape memory and superelasticity of Nitinol are associated with reversible martensitic transformation. This transformation is illustrated in FIG. 4. When the martensite is thermally formed due to cooling it consists of a micro-twinning structure as represented by form 52. Under proper stress or strain conditions the micro-twinning structure undergoes a de-twinning or a realignment process to achieve an energetically stable martensitic state. The micro-twinning and de-twinning process may occur concurrently during the thermal cycling process as shown in FIG. 3. This thermal cycling process illustrated in FIG. 3 can also be called "training". Under this process which includes a constant 1 to 10% strain the de-twinning and realignment results in a stabilized martensitic structure with reduced interfacial friction and residual deformation. This contributes to the greatly improved fatigue resistance that is accomplished according to the processes of this invention.

Figure 6:
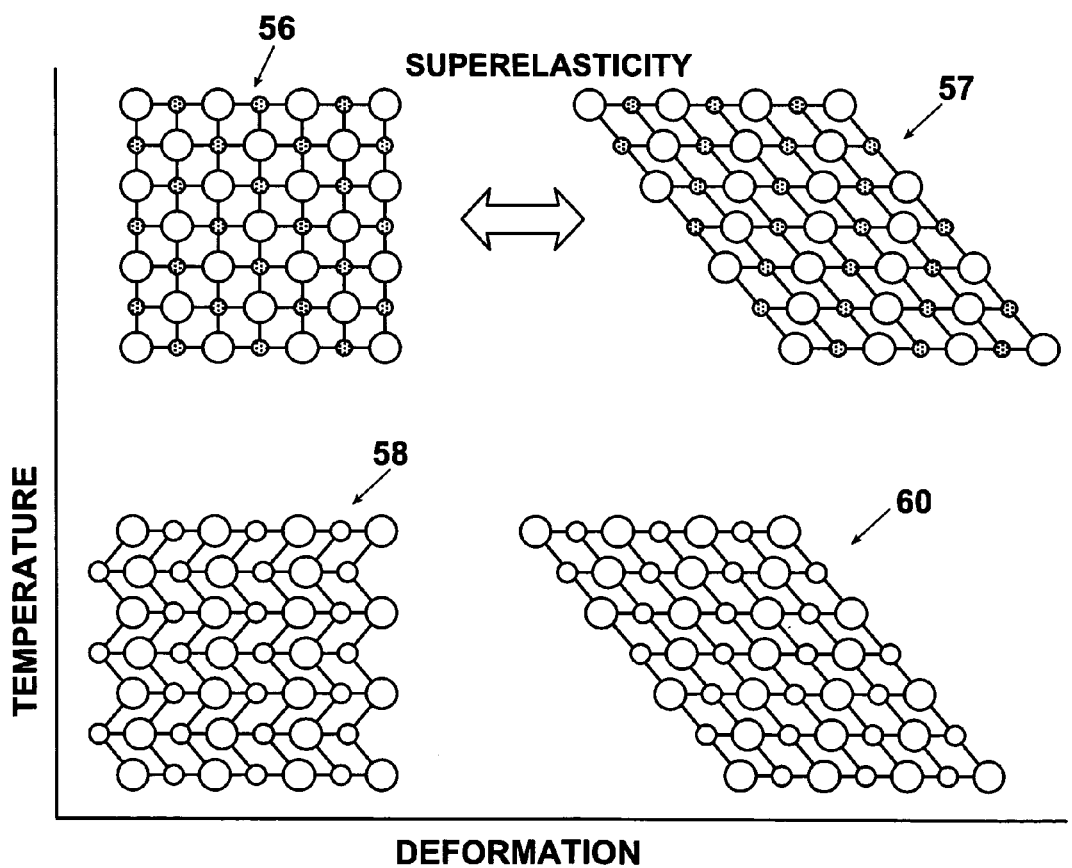
FIG. 6 shows diagrammatically the changes in phases of Nitinol in response to changes in temperature and stress as is shown in FIG. 4 but in somewhat greater detail.

FIG. 6 is a diagram illustrating the temperature versus deformation characteristics of Nitinol. Nitinol has a characteristics of attaining a memorized state indicated by the arrangement of atoms. As shown in FIG. 6, when the temperature of the Nitinol is decreased the atomic structure goes into the twinned martensite state as represented by the numeral 58. While in this reduced temperature state deformation can cause a transformation to a state pictorially illustrated by the numeral 60 which has been defined as the deformed martensite state or de-twinned martensite state.

Again referring to FIG. 6, this diagram illustrates temperature versus deformation showing the superelasticity property of Nitinol. As discussed above with reference to FIG. 5, an alloy element has a shape that is memorized in a state 56 above the critical temperature in which state the alloy is austenitic. This critical temperature is between the $M_s$ and the $M_d$ temperatures. When a strain is applied to the alloy element, the element is deformed to the state 57 in which the alloy element contains large areas of strain-induced martensite. These areas occur primarily at locations at which the highest levels of strain are induced and result in severe deformation that may be unrecoverable. However, at temperatures at which martensite is not the stable phase of the alloy, as soon as the strain is removed, the alloy reverts to an austenitic state 56 and returns to the memorized shape. Superelasticity thus refers to this ability of these alloys while in the austenitic state, to revert to an original shape after severe deformation under strain.

Figure 7:
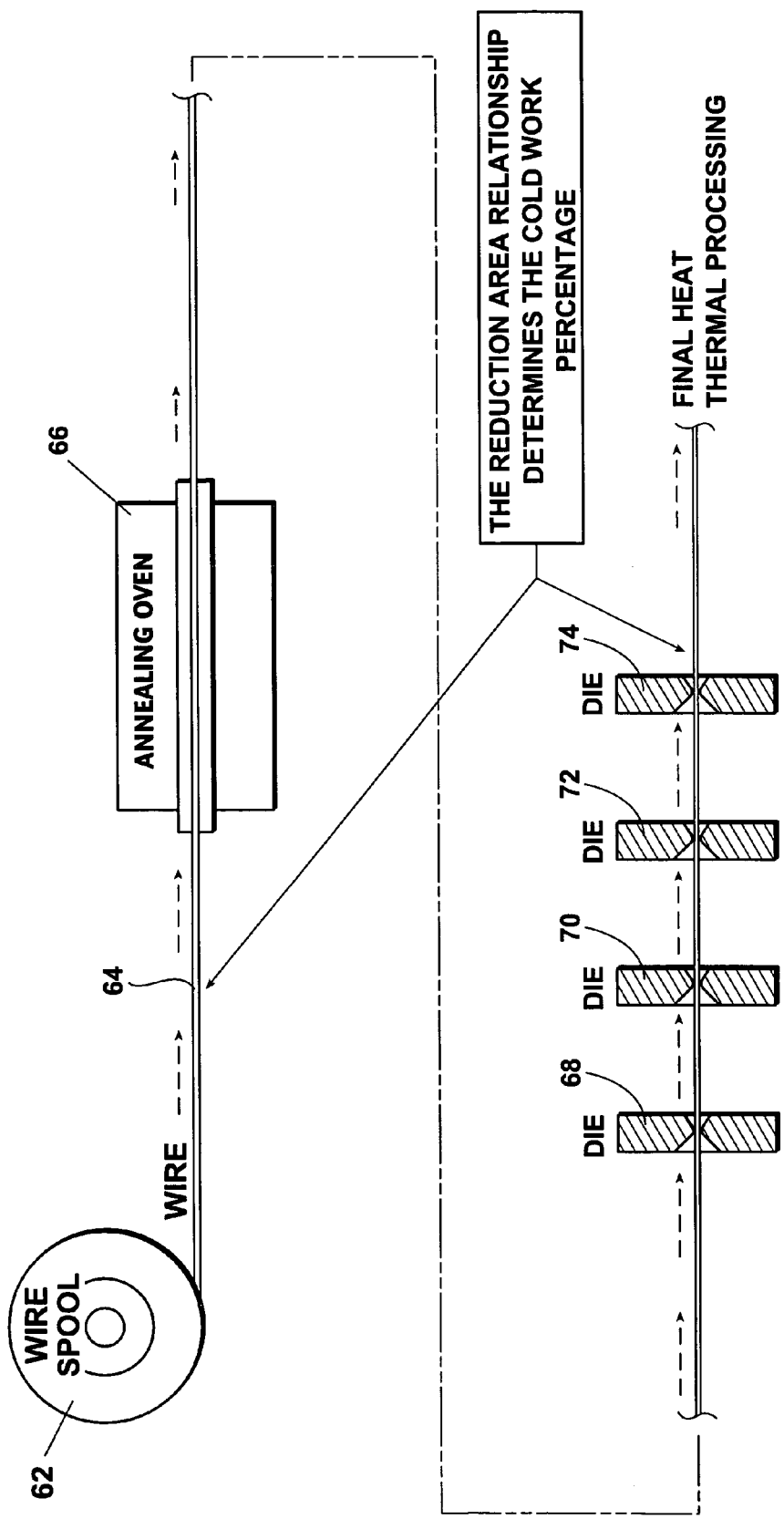
FIG. 7 illustrates an example of cold working procedures that can be employed in preparing Nitinol wire for the final manufacturing steps as shown in FIG. 3.

FIG. 7 illustrates the steps normally employed to convert a Nitinol wire into a stable martensite state useable for manufacturing fatigue resistant devices. From a spool 62, such as would be supplied by a manufacturer of Nitinol alloy products, untreated Nitinol wire 64 passes through an annealing oven 66 and then through a series of dies 68, 70, 72 and 74 to a final heat thermal process. From the final heat thermal process the wire can be placed on a spool, such as spool 28 as seen in FIG. 3. The wire on spool 28 is then in condition for use in the de-twinning or alignment process of FIG. 3. After going through the micro-twinned alignment process of FIG. 3, the wire on finish spool 48 is then in condition for use in manufacturing components or tools, such as the endodontic files that require flexibility and fatigue resistance.

Nitinol treated according to the principles of this invention remains in the martensitic phase even when raised to a temperature above the otherwise critical operating temperature. Therefore, applying additional strain to the alloy does not tend to result in a phase change. Rather, additional strain simply results in a deformation of the alloy which remains in the martensitic phase. The damaging irreversible strain induced from austenite to martensite phase transformation does not take place, and the life of the Nitinol element is substantially increased. In addition, the alloy in the martensite phase is more soft and malleable than when in the austenite phase. Thus martensitic alloy has reduced incidences of stress concentration thereby contributing to the improved fatigue resistance characteristics of the material.

As described above, the shape memory and superelasticity properties of Nitinol and other similar alloys particularly suit them for use in manufacturing medical and dental instruments. The shape memory is useful as it allows an instrument to convert from a first shape to a memorized deployed configuration after being warmed above a critical operating temperature (e.g. by body heat) while superelasticity is useful to allow the instrument to greatly deform while under severe stress in the body, and still return to its original shape.

Nitinol alloy is generally designed to be in the austenitic phase at its operating temperature (i.e., at body temperature), and to be in the martensitic phase at some lower, relatively easy to maintain temperature. The invention herein teaches a method of training a Nitinol instrument to stay in the martensitic phase at body temperature to thereby achieve substantially improved resistance to cyclic fatigue. Specifically, it is desired to improve the fatigue life of Nitinol alloys under conditions where strains (particularly repeated strains) imparted thereto are sufficient to cause phase transformation from austenite to martensite. In addition, it is desired to reduce the formation of fatigue cracks which tend to initiate at the material's stress concentration locations under bending conditions which may occur in a medical device. This is particularly beneficial in the application of Nitinol in the manufacture of endodontic files.

According to the embodiments of the present invention, Nitinol devices are provided that exhibit an increased resistance to fatigue, while retaining their shape memory and superelastic properties. The Nitinol alloy devices according to the invention have an increased ability to withstand cyclic strains, such as may be experienced, for example, in the use of an endodontist file to clean and shape a tooth root canal. Since the Nitinol devices made according to this invention are treated so they tend to remain in the martensitic phase even when the device is at a temperature above the critical operating temperature, applying additional strain does not tend to result in a phase change. Rather, additional strain simply result in the deformation of the alloy while it remains in the martensitic phase. Damaging irreversible strain induced from austenite to martensite phase transformation do not easily take place with Nitinol treated according to the methods of this invention.

Figure 8:
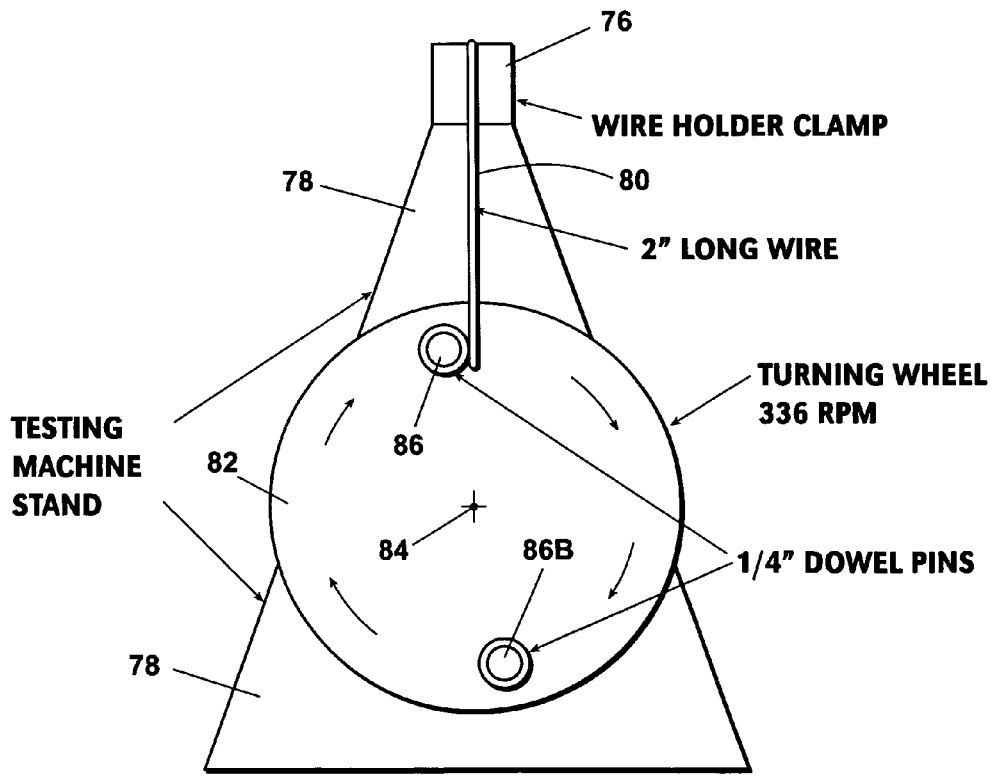
FIG. 8 is a diagrammatic representation of a test machine stand constructed to test the fatigue resistance of Nitinol material, particularly Nitinol material in the form of wire of the type commonly used in the manufacture of instruments including endodontic files.

To verify the integrity of the principles of this invention and to authenticate that by practicing the method of treating Nitinol drawn wire, the structure of which has been trained according to the principles of this invention to remain in the martensite state and to thereby achieve improved fatigue resistance, a test stand as exemplified in FIG. 8 was created. The test stand provides a wire holding clamp 76 that is supported by a test machine stand 78. Secured within wire holding clamp 76 is a length of trained Nitinol wire 80 that has been treated according to the process of this invention. The length of the wire 108 was taken from treated wire 46 as seen in FIG. 3 which is obtained at the conclusion of the manufacturing process as described herein. In this test wire 80 is about 2 inches long and is of a gauge of the type frequently employed for manufacturing endodontic instruments, such as about 1.0 millimeters in diameter.

Rotatably supported to test machine stand 78 if a wheel 82 that rotates about an axis 84. Extending from the face of wheel 82 are two dowel pins 86A and 86B. The dowel pins are typically about one-fourth inch in diameter.

Wheel 82 rotates in a plane which is parallel to the plane of Nitinol wire 80 and in a manner so that the dowel pins 86A and 86B strike the wire and deflect it each time the wheel rotates. In the test utilizing the test stand of FIG. 8, wheel 82 was rotated at a rate of 180 rpm. Since there are two dowel pins 86A and 86B, wire 80 was thereby deflected 360 times a minute. After a dowel pin passes, the wire springs back by its inherent resiliency to extend straight down as indicated in FIG. 8. In summary, the test stand of FIG. 8 deflected the wire 360 times per minute.

Using the test stand of FIG. 8, first a wire that is characterized by the austenitic condition, that is, that had not been subjected to the training procedures of the invention herein as described was tested under room temperature conditions. The wire having austenitic condition failed on the average after about 500 deflections whereas a wire 106 having martensitic conditions as trained by the techniques of this invention on average failed after about 3372 deflections, thus demonstrating the significant fatigue resistance obtained by the method of treating Nitinol drawn wire by this invention.

Figure 9:
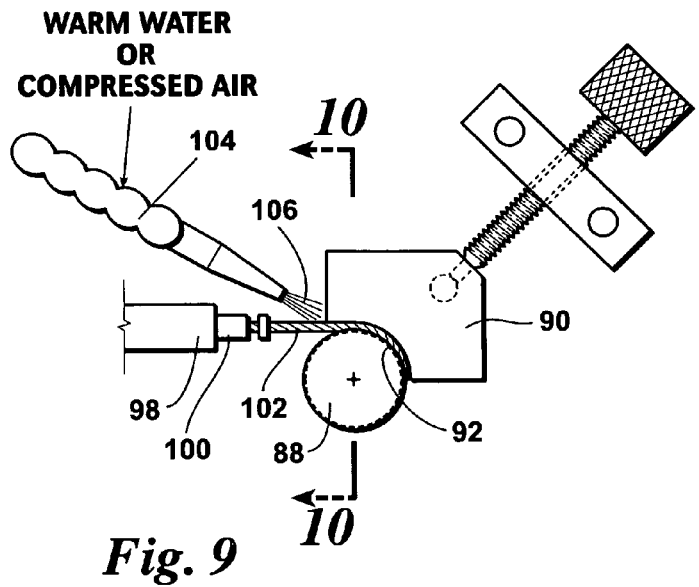
FIG. 9 is a diagrammatic representation of another set up for testing the cyclic fatigue of a finished endodontic file as being representative of products made from Nitinol material utilizing the principles of the present invention.
Figure 10:
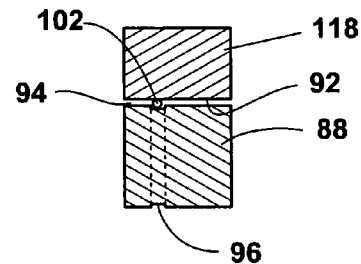
FIG. 10 is a cross-sectional view as taken along the line 10-10 of FIG. 9 showing the relationship of the components employed in the fatigue test of FIG. 9 and showing the position of the endodontic file being tested.

Referring now to FIGS. 9 and 10, a system is illustrated that was designed to test endodontic files to measure fatigue resistance. The test stand of FIG. 9 illustrates diagrammatically a grooved mandrel that is 12 millimeters in diameter. Positioned adjacent the perimeter of mandrel 88 is a deflection block 90 having an arcuate surface 92 concentric to and spaced from the perimeter of mandrel 88. FIG. 10 shows the relationship between the deflection block 90 and the perimeter of mandrel 88 providing a space 94 therebetween. Mandrel 88 has on the peripheral surface a shallow depth groove 96 as seen in FIG. 10.

Supported near deflection block 90 is a rotating instrument holder 98 that has a chuck 100 by which the proximal portion of the shaft of an endodontic instrument 102 can be secured.

Positioned adjacent deflection block 90 is a nozzle 104 that is employed to eject a temperature control medium, such as warm water or compressed air 106 onto endodontic instrument 102. The cyclical fatigue test employing the set up as shown in FIGS. 9 and 10 were conducted wherein the temperature of instrument 102 was maintained wet with warm water at about 37° C., that is about body temperature, to approximate the temperature conditions when an endodontic file is utilized as to clean and shape the root canal of a human tooth. In these tests the endodontic instrument was rotated, that is, spinning counterclockwise at 300 rpm. Rotation of endodontic instrument 102 was continued until it broke as a result of bending fatigue. With instrument 102 having Nitinol austenitic condition the average time to breakage was 85.7 seconds whereas with the instrument being formed of Nitinol having martensitic conditions and having been subjected to the training techniques of this invention as has been described and illustrated, the average time of the breakage was 261 seconds. Thus, utilizing essentially the same Nitinol material first in austenitic condition and then in trained martensitic condition, the fatigue resistance was about three times greater at a testing temperature of 37° C., thus showing a substantial improvement in fatigue resistance by employing the principles of this invention for a tool intended to be utilized at body temperature.

The tests performed as indicated by FIGS. 8, 9 and 10 were not intended to measure improvements in fatigue resistance under all conceivable conditions, but have been carried out sufficient to graphically demonstrate the significant improvement in fatigue resistance of Nitinol material when a martensitic condition is maintained employing the training and principles of the invention as illustrated and described herein.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of treating nickel titanium drawn wire to train the structure thereof to resist cyclic fatigue comprising the steps of:
    subjecting the wire to elongational strain of between 1% to 10% to stabilize the atomic structure thereof; and
    while subjected to said elongational strain, thermally cycling the wire between cold and hot baths for a minimum of about three cycles,
wherein the cold bath is at about 0° C. to 10° C. and the hot bath is at about 100° C. to 180° C.

2. A method according to claim 1 wherein the cold bath employs water sprayed on the wire.

3. A method according to claim 1 wherein the hot bath employs a pool of water within which the wire travels.

4. A method of manufacturing an instrument from a nickel titanium blank to obtain improved fatigue failure characteristics, comprising:
    training the nickel titanium blank by repeatedly subjecting the blank to temperature changes while simultaneously applying elongational strain deformation to the blank within its reversible strain limit to obtain a nickel titanium blank in a trained state; and
    forming an instrument by machining operations while maintaining said blank in the trained state,
    wherein said step of training the nickel titanium blank includes repeatedly subjecting the blank to temperature changes between a first temperature of about 0° C. to 10° C. and a second temperature of about 100° C. to 180° C.

5. A method of manufacturing an instrument from a nickel titanium blank according to claim 4 wherein said step of training the nickel titanium blank includes subjecting the blank alternatively to cold and hot water environments.

6. A method of manufacturing an instrument from a nickel titanium blank according to claim 5 wherein said water environments are selected from water spray and water bath environments.

7. A method of manufacturing an instrument from a nickel titanium blank according to claim 4 wherein said strain deformation is applied at a rate to stretch the nickel titanium blank from about 1% to about 10%.

8. A method of manufacturing an instrument from a nickel titanium blank according to claim 4 wherein said blank is in the form of wire.

9. A method of manufacturing an instrument from a nickel titanium blank according to claim 4 wherein said blank is in the form of wire that has been drawn repeatedly to achieve a cross-sectional area reduction of about 40%.

10. A method of treating nickel titanium drawn wire to achieve improved fatigue resistance comprising the steps of:
subjecting the wire to a strain to stabilize the atomic structure thereof; and
while subjected to strain, thermally cycling the wire between cold and hot baths for a minimum of about three cycles;
wherein the cold bath is at about 0° C. to 10° C. and the hot bath is at about 100° C. to 180° C.

11. A method according to claim 10 wherein the cold bath employs water sprayed on the wire.

12. A method according to claim 10 wherein the hot bath employs a pool of water within which the wire travels.

* * * * *